United States Patent
Ávila Zaragozá et al.

(10) Patent No.: US 8,236,778 B2
(45) Date of Patent: Aug. 7, 2012

(54) SYNERGISTIC 5'-METHYLTHIOADENOSINE COMBINATIONS

(75) Inventors: Matías Antonio Ávila Zaragozá, Pamplona-Navarra (ES); Fernando José Corrales Izquierdo, Pamplona-Navarra (ES); Begoña Fernández Díez, Pamplona-Navarra (ES); Beatriz Moreno Bruna, Pamplona-Navarra (ES); Pablo Villoslada Díaz, Pamplona-Navarra (ES)

(73) Assignee: Proyecto de Biomedicina Cima, S.L., Pamplona, Navarra (ES)

( * ) Notice: Subject to any disclaimer, the term of this patent is extended or adjusted under 35 U.S.C. 154(b) by 77 days.

(21) Appl. No.: 12/922,980

(22) PCT Filed: Mar. 18, 2009

(86) PCT No.: PCT/ES2009/070067
§ 371 (c)(1),
(2), (4) Date: Sep. 16, 2010

(87) PCT Pub. No.: WO2009/115634
PCT Pub. Date: Sep. 24, 2009

(65) Prior Publication Data
US 2011/0015132 A1  Jan. 20, 2011

(30) Foreign Application Priority Data
Mar. 19, 2008  (ES) .................................. 200800806

(51) Int. Cl.
*A61K 31/70* (2006.01)
*C07H 19/167* (2006.01)
(52) U.S. Cl. ...................... 514/46; 424/280.1; 536/27.3
(58) Field of Classification Search ........................ None
See application file for complete search history.

(56) References Cited

U.S. PATENT DOCUMENTS
7,820,637 B2   10/2010   Diaz et al.

FOREIGN PATENT DOCUMENTS
WO   9941247        8/1999
WO   2006097547 A1  9/2006

OTHER PUBLICATIONS

Boggild, M., Rationale and experience with combination therapies in multiple sclerosis, J Neurol, 2006, pp. VI/45-VI/51, vol. 253, suppl. 6.
Costello, F., et al., Combination therapies for multiple sclerosis: scientific rationale, clinical trials, and clinical practice, Current Opinion in Neurology, 2007, pp. 281-285, vol. 20.
Gold, R., Combination therapies in multiple sclerosis, J Neurol, 2008, pp. 51-60, vol. 255, suppl. 1.
Ramtahal, J., et al., Sequential maintenance treatment with glatiramer acetate after mitoxantrone is safe and can limit exposure to immunosuppression in very active, relapsing remitting multiple sclerosis, J Neurol, 2006, pp. 1160-1164, vol. 253.
Stüve, O., et al., Immunomodulatory synergy by combination of atorvastatin and glatiramer acetate in treatment of CNS autoimmunity, The Journal of Clinical Investigation, Apr. 2006, pp. 1037-1044, vol. 116, No. 4.
Williams-Ashman, H.G., et al., Trends in the Biochemical Pharmacology of 5'-Deoxy-5'-Methylthioadenosine, Biochemical Pharmacology, 1982, pp. 277-288, vol. 31, No. 3.

*Primary Examiner* — John Ulm
(74) *Attorney, Agent, or Firm* — Andrew D. Gerschutz; Tristan A. Fuierer; Moore & Van Allen, PLLC

(57) ABSTRACT

The present invention relates to combinations of 5'-methylthioadenosine and glatiramer acetate, and to their use in the treatment of multiple sclerosis. In a particular embodiment, the present invention relates to a product comprising 5'-methylthioadenosine and glatiramer acetate as a combined preparation for the simultaneous, separate, or sequential use thereof for the prevention and/or treatment of multiple sclerosis.

10 Claims, 1 Drawing Sheet

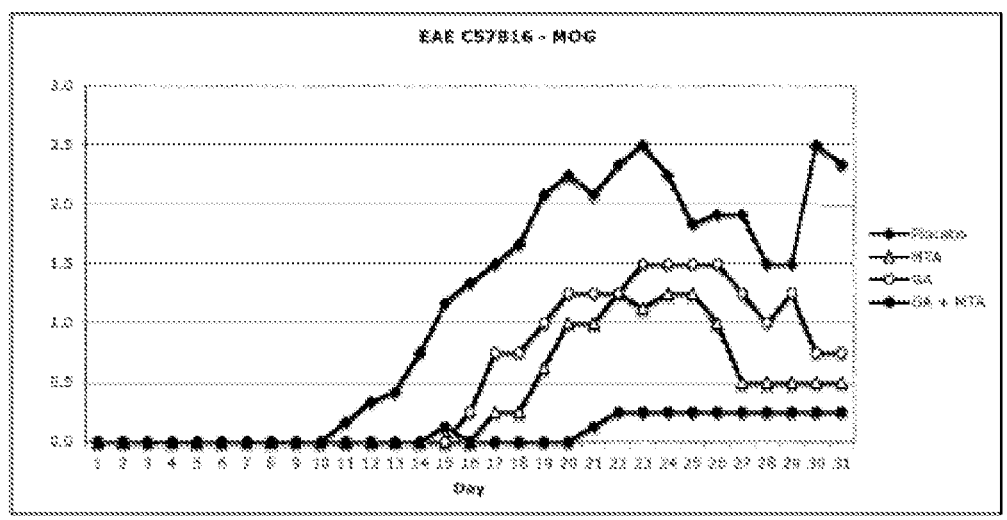

SYNERGISTIC 5'-METHYLTHIOADENOSINE COMBINATIONS

CROSS-REFERENCE TO RELATED APPLICATIONS

This application is filed under the provisions of 35 U.S.C. §371 and claims the priority of International Patent Application No. PCT/ES2009/070067 filed on 18 Mar. 2009 entitled "Synergistic 5'-Methylthioadenosine Combinations" in the name of Matías Antonio Ávila Zaragozá, et al., which claims priority of Spanish Patent Application No. P200800806 filed on 19 Mar. 2008, both of which are hereby incorporated by reference herein in their entirety.

FIELD OF THE INVENTION

The present invention relates to combinations of 5'-methylthioadenosine and glatiramer acetate, and to their use in the prevention and/or treatment of multiple sclerosis. In a particular embodiment, the invention relates to a product comprising 5'-methylthioadenosine and glatiramer acetate as a combined preparation for the simultaneous, separate, or sequential use thereof for the prevention and/or treatment of multiple sclerosis.

BACKGROUND OF THE INVENTION

Multiple sclerosis (MS) is an autoimmune disease currently affecting two million people around the world, mainly in well developed countries, with an important inflammatory component.

Six medicaments are currently approved for the treatment of relapsing forms of MS, including: three interferon-β preparations [Avonex (interferon beta-1a) (Biogen Idec, Cambridge, Mass., United States), Betaseron®/Betaferon® (interferon beta-1b) (Berlex, Montville, N.J., United States), and Rebif® (Serono, Geneva, Switzerland)]; glatiramer acetate (GA) (Copaxone®; Teva, Nordani, Israel); mitoxantrone (Novantrone®; Serono, Geneva, Switzerland); and natalizumab (Tysabri®; Biogen Idec) [Jacobs et al. Ann Neurol (1996), 39:285-294; IFNβ Multiple Sclerosis Study Group. Interferon beta-1b is effective in relapsing remitting multiple sclerosis. I. Clinical results of a multicenter, randomized, double-blind, placebo-controlled trial. Neurology (1993), 43:655-661; PRISMS (Prevention of Relapses and Disability by Interferon beta 1a Subcutaneously in Multiple Sclerosis) Study Group. Lancet (1998), 352:1498-1504. Johnson et al. Neurology (1995); 45:1268-1276. Hartung et al. Lancet (2002), 360:2018-2025 Polman et al. N Engl J Med (2006), 354:899-910]. Interferons-β and glatiramer acetate act as first-line agents, and have been routinely used for approximately a decade. The drawback of these approved anti-MS drugs is that they need to be administered subcutaneously (Interferon-beta or GA), intramuscularly (interferon beta-1a) or intravenously (Natalizumab).

The pathophysiology of MS is multifaceted and it may be necessary to combine different drugs with complementary mechanisms of action to obtain maximal clinical benefit in patients who do not respond to conventional monotherapies. The main clinical rationale for using drug combinations is obtaining additive or even synergistic therapeutic effects [Reid. J Hum Hypertens (1995), 9 (Suppl 4):S19-S23]. There are two pharmacological bases for using a combination of two or more drugs: Class 1 combination therapies include two (or more) drugs that are considered independent from one other and target different aspects of the harmful mechanisms underlying the disease [Toews et al. Proc Am Thorac Soc 2005; 2:282-289]. In the case of MS, for example, one drug may target cell traffic in the CNS, whereas another drug may affect cell activation. Class 2 drug combinations include two or more pharmacological agents that have different molecular targets within a single cell type, or a single response mechanism in that cell type [Toews et al. (2005) mentioned above].

Glatiramer acetate, also known as Copolymer 1, Cop 1, copaxone, or GA, is a non-pathogenic synthetic random copolymer made up of the four amino acids: L-Glu, L Lys, L-Ala, and L-Tyr. It has been described that, due to its different mechanisms of action, glatiramer acetate may represent the ideal candidate to accompany other agents to achieve complementary and potentially synergistic therapeutic effects (Costello et al. Curr Op Neurology (2007), 20:281-285). Boggild [Boggild. J Neurol (2006), 253 (Suppl 6):VI/45-VI/51] and Ramtahal et al. [Ramtahal et al. J Neurol (2006); 253:1160-1164] used mitoxantrone as an induction therapy followed by maintenance therapy with GA in a series of non-random, uncontrolled observational cases, and observed a 90% reduction in the relapse rate among patients. WO2005009333 describes that Copolymer 1 (GA)-related heteropolymers or peptides in combination with other immunosuppressive drugs induce an unexpected synergistic effect, and thus improve the efficacy of the current immunosuppressive regimens.

Unfortunately, therapy with GA has some drawbacks deriving from its required fixed dose and the fact that the response is highly sensitive to the specific regimen of administration, requiring daily doses in order to achieve its efficacy. Furthermore, due to its vaccine design, the individual immune responses after GA immunization differ between individuals depending on the genetic background or other immunological factors, leading to a range of different degrees of responders. In fact, the current efficacy of GA in preventing new relapses in MS is not more than 25%. This limited efficacy prevents its widespread use in several countries and it is often prescribed for patients with a mild disease; patients with a more severe disease are frequently not treated with GA. As such, GA is nowadays only approved for the treatment of relapsing-remitting MS.

5'-methylthioadenosine (MTA) is a lipophilic sulfur-containing adenine nucleoside produced from S-adenosylmethionine (SAM) during the synthesis of the polyamines spermine and spermidine. MTA is capable of preventing acute Experimental Autoimmune Encephalomyelitis (EAE) and ameliorates Chronic-Relapsing EAE (RR-EAE), two different models of Multiple Sclerosis (MS), by means of the modulation of T cell activation, the decrease of inflammation and demyelination in the central nervous system [Moreno et al. Ann. Neurol. (2006) September, 60(3):323-334]. MTA has shown a dose-response effect with a wide range of doses without side effects. Furthermore, MTA is a suitable drug for oral formulations due to its small size and hydrophilic character. EP352609 describes the use of adenosine derivatives, particularly MTA, in preparing pharmaceutical compositions possessing immunostimulant activity. WO2006097547 describes the use of MTA in the prevention and/or treatment of autoimmune diseases, such as MS, and in the prevention and/or treatment of transplant rejection.

The mechanisms of action through which MTA exerts its immunomodulatory activity are complex [Williams-Ashman et al., Biochem Pharmacol. (1982), 31:277-288]. Nevertheless, it can be asserted that MTA specifically modulates the immune responses dependent on CD4+ cell activation through the chemical modulation of the signaling pathways.

GA has shown a competitive activity for the binding of the T-cell receptor specific for the Myelin Basic Protein (MBP). GA can be considered as a vaccine for inducing immune tolerance against brain self-antigens. It has been observed that therapy with GA induces a shift towards Th2 responses and the activation of regulatory T-cells that suppress the autoimmune response. Due to its vaccine-type mechanism of action, in order to be effective GA needs to induce an immune response against GA mediated by CD4+. Since MTA suppresses CD4+ activation, which is necessary for the generation of GA-specific T cell responses, it could be expected that the combination of MTA and GA could be neutral or even harmful.

SUMMARY OF THE INVENTION

Despite what could be expected, it has now been surprisingly found that the combined administration of MTA and GA to an MS animal model gives rise to a more potent immunomodulatory activity compared to the administration of each of the drugs separately. As such, the combined administration of MTA and GA has proven to be useful in decreasing the harmful effects of MS, and is therefore, a valuable therapy in the prevention and treatment of MS.

Furthermore, the combination of MTA and GA has several advantages since it can overcome the individual and limited efficacy of GA. The combination of MTA and GA further allows a flexible dosage regimen, which will increase the opportunities for having a good control of the disease and expanding its indication for a broader group of patients, allowing an individualized therapy by means of adjusting dosage regimens to the specific needs of a certain patient. Furthermore, since MTA can be administered orally, the combination therapy of GA and MTA is clearly beneficial as regards the improvement of the quality of life of the patient as the amount of injections to be administered to him or her decreases.

Therefore, in one aspect, the present invention relates to a combination comprising (A) MTA and/or the pharmaceutically acceptable salts and/or prodrugs thereof, and (B) glatiramer acetate. Expressed in an alternative manner, the invention relates to a product comprising (A) MTA and/or the pharmaceutically acceptable salts and/or prodrugs thereof, and (B) GA, as a combined preparation.

In another aspect, the present invention relates to a pharmaceutical composition comprising said combination comprising (A) MTA and/or the pharmaceutically acceptable salts and/or prodrugs thereof, and (B) GA.

In another aspect, the present invention relates to a product comprising, separately, (A) MTA and/or the pharmaceutically acceptable salts and/or prodrugs thereof, and (B) GA, as a combined preparation for the simultaneous, separate, or sequential use thereof in the prevention and/or treatment of multiple sclerosis.

The combination, pharmaceutical composition or product referred to above are particularly useful in the prevention and/or treatment of MS, particularly, of a relapsing form of MS, more particularly a relapsing-remitting form of MS, even more particularly, of a relapsing-remitting form of MS with the presence of one or more relapses after being treated with GA alone for at least 6 months.

DESCRIPTION OF THE DRAWINGS

The FIGURE is a graph showing the chronological score of the severity of the EAE disease developed by C57/bl6 mice treated daily with placebo, MTA, GA or MTA+GA

DESCRIPTION OF THE INVENTION

Definitions

The term "and/or" refers to a nonexclusive "or", i.e., "A and/or B" includes both "A and B" as well as "A or B". As such, the phrase MTA and/or the pharmaceutically acceptable salts and/or prodrugs thereof, refers to MTA alone, as well as to a pharmaceutically acceptable salt of MTA alone, and to a prodrug of MTA alone, or to the combinations thereof.

The term "therapeutically effective amount" means an amount of a compound or combination of compounds that treats a disease; ameliorates, attenuates, or eliminates one or more symptoms of a particular disease; or prevents or delays the onset of one of more symptoms of a disease.

The term "pharmaceutically acceptable" means that a compound or combination of compounds is compatible with the other ingredients of a formulation, and not harmful for the patient.

The term "pharmaceutically acceptable salts", as used herein, refers to any salt of MTA which can be used in the manufacture of a medicament. The nature of the salt is not critical provided that it is not toxic and is pharmaceutically acceptable. Among the pharmaceutically acceptable salts of MTA are acid addition salts, which can be obtained from organic or inorganic acids by conventional methods well known by persons skilled in the art by reacting the appropriate acid with MTA in the suitable stoichiometric amount. Illustrative non-limiting examples of organic acids which can be used to obtain said acid addition salts include acetic acid, p-aminosalicylic acid, ascorbic acid, benzenesulfonic acid, citric acid, 1,4-butanesulfonic acid, cyclamic acid, ethanesulfonic acid, fumaric acid, hydroxyacetic acid, lactic acid, maleic acid, malic (hydroxybutanedioic) acid, malonic acid, methanesulfonic acid, oxalic (ethanedioic) acid, pamoic acid, pyruvic acid, propanoic acid, salicylic acid, succinic (butanedioic) acid, tartaric acid, p-toluenesulfonic acid and similar acids. Likewise, illustrative non-limiting examples of inorganic acids which can be used to obtain said acid addition salts include, for example, hydrochloric acid, hydrobromic acid, sulfuric acid, nitric acid, phosphoric acid and similar acid. By way of illustration, for example, MTA hydrochloride can be used in injectable formulations; MTA hydrochloride, MTA sulfate, MTA citrate, MTA ascorbate, MTA 1,4-butanedisulfonate (gastro-resistant tablets), MTA p-toluenesulfonate, etc. can be used in oral formulations. For their therapeutic use, the therapeutically acceptable salts of MTA are administered in pharmaceutically acceptable concentrations. The addition salts of MTA can be converted by means of treatment with a suitable base into the free base form.

The term "prodrug", as used herein, includes any compound derived from MTA which, when it is administered to a subject, is capable of providing MTA, directly or indirectly, to said subject. Illustrative non-limiting examples of said prodrugs of MTA include the acylated (e.g., acetylated or other) derivatives thereof, the esters thereof (e.g., the pyridine esters thereof or others), etc (WO98/16184). Advantageously, said derivative of MTA is a compound increasing the bioavailability of MTA when it is administered to a subject or enhancing the release of MTA in a biological compartment. The nature of said derivative is not critical provided that it can be administered to a subject and that it provides MTA in a biological compartment of said subject. Said prodrug can be prepared by conventional methods known by persons skilled in the art.

The term "preventing" refers to keep from happening, occurring, or alternatively delaying the onset or recurrence of a disease, disorder, or condition to which such term applies, or of one or more symptoms associated with a disease, disorder, or condition. The term "prevention" refers to the act of preventing, which has already been defined above.

The term "treating", as used in the present invention, refers to reversing, alleviating, or inhibiting the progress of the disorder or condition to which such term applies, or one or more symptoms of such disorders or condition. The term "treatment" refers to the act of treating, which has already been defined above.

The term "subject" means animals, particularly mammals such as dogs, cats, cows, horses, sheep, geese, and humans. Particularly preferred patients are mammals, including humans of both sexes.

A sclerosis is a progressive hardening, or hardening, and refers especially to the hardening of a tissue due to inflammation and to the increased formation of connective tissue and in diseases of the interstitial substance. The term "sclerosis" is mainly used for such hardening of the nervous system due to the deposition of connective tissue, or to designate the hardening of blood vessels.

Multiple sclerosis (MS) is a disease in which there are demyelination foci of several sizes throughout the white matter of the CNS, sometimes extending into the gray matter, giving rise weakness, incoordination, paresthesias, speech disorders, and visual complaints. MS is a disease of unknown etiology with a prolonged course involving many remissions and relapses. The term "multiple sclerosis" or "MS", as used herein, is meant to include benign multiple sclerosis (benign MS), relapsing-remitting multiple sclerosis (RRMS), secondary progressive multiple sclerosis (SPMS), primary progressive multiple sclerosis (PPMS), and progressive-relapsing multiple sclerosis (PRMS). These subtypes or forms of the disease (MS) may be distinguished from one another on the basis of the course of the disease, of the type of inflammation involved, and through the use of magnetic resonance imaging (MRI).

Chronic progressive multiple sclerosis is a term used to collectively refer to SPMS, PPMS, and PRMS. The relapsing forms of multiple sclerosis are SPMS with superimposed relapses, RRMS, and PRMS.

MTA, (5'-methylthioadenosine) [CAS registration number: 2457-80-9], has the following structural formula:

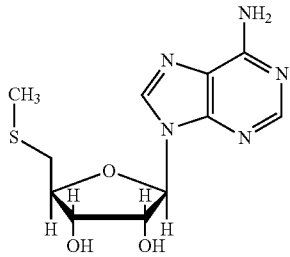

MTA is a commercial product that can be provided by the company Sigma. Alternatively, this compound can be obtained by known processes, for example, from S-adenosylmethionine (SAM) according to the process described by Schienk F. et al., Arch. Biochem. Biophys., 1964, 106:95-100.

Copaxone® is the trade name for a formulation containing glatiramer acetate (GA) as the active ingredient. Glatiramer acetate is approved for reducing the frequency of relapses in relapsing-remitting multiple sclerosis (RRMS). GA is a synthetic copolymer made up of four naturally occurring amino acids: L-glutamic acid, L-alanine, L-tyrosine, and L-lysine with an average molar ratio in Copaxone® of 0.141, 0.427, 0.095 and 0.338, respectively. In Copaxone®, the average molecular weight of GA is 4,700-11,000 daltons. Chemically, GA is designated as L-glutamic acid polymer with L-alanine, L-lysine and L-tyrosine, acetate (salt); its CAS registration number is 147245-92-9 and its structural formula is:

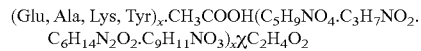

GA is commercially available from Advanced Technology, Finechemie & Pharma, ACC Corp Product, Accurate Chemical And Scientific, Aceto, or China Hallochem Pharma Co., Ltd.

Combination of MTA and GA

In one aspect, the present invention relates to a combination, hereinafter combination of the invention, comprising:
(A) 5'-methylthioadenosine and/or the pharmaceutically acceptable salts and/or prodrugs thereof, and
(B) glatiramer acetate.

Said combination of the present invention is particularly useful for preventing and/or treating multiple sclerosis (MS) in any of its forms.

As used herein, the "combination of the invention" is a combined composition in which its components can be provided according to different alternative presentations. In a particular embodiment, the combination of the invention is presented as a product or kit comprising the components [(A) and (B)] of the combination in one, two or more packs, and optionally, other components or elements (e.g., vials, syringes, etc.); said product or kit can be, among others, a one pack composition or a two pack composition. The combination of the invention is suitable as a combined preparation for simultaneous, separate and/or sequential use in the prevention and/or treatment of multiple sclerosis.

Therefore, expressed in an alternative manner, the invention relates to a product comprising: (A) 5'-methylthioadenosine (MTA) and/or the pharmaceutically acceptable salts and/or prodrugs thereof, and (B) glatiramer acetate (GA), as a combined preparation.

In a particular embodiment, the combination of the invention can additionally comprise one or more additional compounds useful in the treatment of MS, such as an interferon-beta (e.g., interferon beta-1a, interferon beta-1b, etc.), mitoxantrone, natalizumab, fingolimod, laquinimod, rituximab, daclizumab, fampridine, sativex, alemtuzumab, fumaric acid, teriflunomide, cladribine, mycophenolate mofetil, ibudilast, atacicept, etc.

Given that the combination of the invention is particularly suitable for the prevention and/or treatment of MS in any of its forms, said combination of the invention can be used as a medicament.

Therefore, in another aspect, the invention relates to the use of said combination of the invention in the manufacture of a medicament for preventing and/or treating multiple sclerosis. In other words, the present invention provides a combination of the invention for the use thereof in the prevention and/or treatment of MS in a subject, i.e., the present invention provides a product comprising, separately, (A) MTA and/or the pharmaceutically acceptable salts and/or prodrugs thereof, and (B) GA, as a combined preparation for the simultaneous, separate or sequential use thereof in the prevention and/or treatment of multiple sclerosis.

In equivalent terms, the present invention comprises a process for the prevention and/or treatment of MS comprising administering to a subject in need of such prevention and/or treatment an effective amount of a combination of the invention.

In a particular embodiment of the present invention, the combination of the invention is used for the prevention and/or treatment of any form of multiple sclerosis, i.e. benign multiple sclerosis, RRMS, SPMS, PPMS and PRMS. In a preferred embodiment of the present invention, the combination of the invention is useful in the prevention and/or treatment of relapsing forms of MS, i.e., RRMS and PRMS. In a more preferred embodiment of the present invention, the combination of the invention is useful in the prevention and/or the treatment of relapsing-remitting forms of MS, particularly RRMS. In an even more preferred embodiment of the present invention, the combination of the invention is useful in the prevention and/or treatment of subjects with RRMS, with the presence of one or more relapses after having been treated with GA alone for at least 1 month, 2 months, 3 months, 4 months, 5 months, 6 months, 7 months, 8 months, 9 months, 10 months, 11 months, or 12 months. In another preferred embodiment, the combination of the invention is useful in the prevention and/or treatment of subjects who suffer from MS and who have finished a therapy of mitoxantrone with GA.

The amount of MTA and/or the pharmaceutically acceptable salts thereof, when taken alone, as well as the amount of GA when taken alone, is usually effective to alleviate the symptoms of any of the forms of MS (i.e., the treatments are partially effective). Alternatively, the amount of MTA and/or the pharmaceutically acceptable salts and/or prodrugs thereof, when taken alone, or the amount of GA when taken alone, may not be effective to alleviate the symptoms of any of the forms of MS (i.e., the individual treatments are not effective but they are effective when combined).

The dose of MTA and/or the pharmaceutically acceptable salts and/or prodrugs thereof and GA to be administered depends on the individual case and, as is usual, must be adapted to the conditions of the individual case for an optimum effect. Therefore, it naturally depends on the frequency of administration and on the potency and duration of action of the compounds used in each case for therapy or prophylaxis, but also on the nature and severity of the disease and symptoms, and on the sex, age, weight, joint medication (co-medication) and individual sensitivity of the subject to be treated and on whether the therapy is acute or prophylactic.

The therapeutically effective amount of MTA and/or the pharmaceutically acceptable salts and/or prodrugs thereof may generally be comprised in the range from 0.01 mg to 50 g per day; from 0.02 mg to 40 g per day; from 0.05 mg to 30 g per day; from 0.1 mg to 20 g per day; from 0.2 mg to 10 g per day: from 0.5 mg to 5 g per day; from 1 mg to 3 g per day; from 2 mg to 2 g per day; from 5 mg to 1.5 g per day; from 10 mg to 1 g per day; or from 10 mg to 500 mg per day.

The therapeutically effective amount of GA may be comprised in the range from 50 to 150 mg/day: from 60 to 140 mg/day; from 70 to 130 mg/day; from 80 to 120 mg/day; from 90 to 110 mg/day; or is 100 mg/day. Likewise, in another particular embodiment, the amount of glatiramer acetate may be comprised in the range from 10 to 80 mg/day; from 12 to 70 mg/day; from 14 to 60 mg/day; from 16 to 50 mg/day; from 18 to 40 mg/day; from 19 to 30 mg/day; or is approximately 20 mg/day.

The administration of GA is carried out on a daily regimen basis, alternatively on a twice daily regimen, administering half the daily amount to be administered in each regimen. In an alternative particular embodiment, the periodic administration of GA is carried out once every 3 to 11 days; once every 5 to 9 days; once every 7 days; or once every 24 hours.

For each administration regimen of GA, MTA and/or the pharmaceutically acceptable salts and/or prodrugs thereof may be administered once every 6 to 24 hours; once every 7 to 22 hours; once every 8 to 20 hours; once every 9 to 18 hours; once every 10 to 16 hours; once every 11 to 14 hours; or once every 12 hours.

MTA and/or the pharmaceutically acceptable salts and/or prodrugs thereof and GA may be administered together, either as separate pharmaceutical formulations or as part of the same unit dosage form. Alternatively, MTA and/or the pharmaceutically acceptable salts and/or prodrugs thereof and GA may be administered separately but as part of the same therapeutic regimen. The two components, if administered separately, need not necessarily be administered at essentially the same time, although they can if so desired. Thus, MTA and/or the pharmaceutically acceptable salts and/or prodrugs thereof and GA may be administered as separate doses or dosage forms, but at the same time. Optionally, the separate administration of MTA and/or the pharmaceutically acceptable salts and/or prodrugs thereof and GA may be carried out at different times and in any order.

In a particular embodiment of the present invention, the administration of the GA substantially precedes the administration of MTA and/or the pharmaceutically acceptable salts and/or prodrugs thereof. Alternatively, the administration of MTA and/or the pharmaceutically acceptable salts and/or prodrugs thereof substantially precedes the administration of GA.

In another particular embodiment of the present invention, GA and MTA and/or the pharmaceutically acceptable salts and/or prodrugs thereof may be administered for a period of time of at least 4 days. In an additional embodiment, the period of time may be from 5 days to 5 years; from 10 days to 3 years; from 2 weeks to 1 year; from 1 month to 6 months; or from 3 months to 4 months. In another particular embodiment, GA and MTA and/or the pharmaceutically acceptable salts and/or prodrugs thereof may be administered for the lifetime of the subject.

MTA and/or the pharmaceutically acceptable salts and/or prodrugs thereof, as well as GA, may be administered, independently from one another, by any suitable route, for example, by oral, nasal, pulmonary, parenteral, intravenous, intra-articular, transdermal, intradermal, subcutaneous, topical, intramuscular, rectal, intrathecal, intraocular, buccal route or by means of gavage. The route of administration of MTA and/or the pharmaceutically acceptable salts and/or prodrugs thereof, is preferably the oral route or by means of gavage. The preferred route of administration for GA is the subcutaneous or oral route. A person skilled in the art will recognize that doses at the highest end of the range may be necessary for oral administration.

In a particular embodiment, GA may be administered by subcutaneous, intraperitoneal, intravenous, intramuscular, intraocular or oral route, and the administration of MTA and/or the pharmaceutically acceptable salts and/or prodrugs thereof may be oral. In another particular embodiment, the administration of GA may be subcutaneous and the administration of MTA and/or the pharmaceutically acceptable salts and/or prodrugs thereof, may be oral.

In another aspect, the present invention relates to a pharmaceutical composition, hereinafter pharmaceutical composition of the invention comprising a therapeutically effective amount of a combination of the invention, comprising (A) MTA and/or the pharmaceutically acceptable salts and/or prodrugs thereof, and (B) GA, and a pharmaceutically acceptable excipient.

In a particular embodiment, the amount of GA when taken alone, as well as the amount of MTA and/or the pharmaceutically acceptable salts and/or prodrugs thereof, when taken alone, in the pharmaceutical composition of the invention, is effective to alleviate the symptoms of multiple sclerosis (i.e., the individual treatments are partially effective). Alternatively, the amount of glatiramer acetate when taken alone, or the amount of MTA and/or the pharmaceutically acceptable salts and/or prodrugs thereof, when taken alone, may not be effective to alleviate the symptoms of multiple sclerosis in any of its forms (i.e., the individual treatments are not effective but they are effective when combined). The amount of GA in the pharmaceutical composition of the invention may coincide with the therapeutically effective daily dose and may be comprised in the range from 10 to 80 mg, from 12 to 70 mg, from 14 to 60 mg, from 16 to 50 mg, from 18 to 40 mg, from 19 to 30 mg, or is approximately 20 mg. Alternatively, in another particular embodiment, the amount of GA in the pharmaceutical composition may be comprised in the range from 50 to 150 mg, from 60 to 140 mg, from 70 to 130 mg, from 80 to 120 mg, from 90 to 110 mg, or is approximately 100 mg.

For each amount of GA in the pharmaceutical composition of the invention, the amount of MTA and/or the pharmaceutically acceptable salts and/or prodrugs thereof, in the pharmaceutical composition of the invention may be comprised in the range from 0.01 mg to 50 g, from 0.02 mg to 40 g, from 0.05 mg to 30 g, from 0.1 mg to 20 g, from 0.2 mg to 10 g, from 0.5 mg to 5 g, from 1 mg to 3 g, from 2 mg to 2 g, from 5 mg to 1.5 g, from 10 mg to 1 g, from 10 mg to 500 mg.

In a preferred embodiment of the present invention, the pharmaceutical composition of the invention is intended for its subcutaneous, intraperitoneal, intravenous, intramuscular or intraocular administration.

In another aspect, the invention relates to a product, hereinafter product of the invention, comprising MTA and/or the pharmaceutically acceptable salts and/or prodrugs thereof and GA as a combined preparation for the simultaneous, separate, or sequential use thereof in the prevention and/or treatment of MS.

In another aspect, the present invention further relates to a kit, hereinafter kit of the invention, comprising a combination of separate pharmaceutical compositions, wherein at least one of said pharmaceutical compositions comprises MTA and/or the pharmaceutically acceptable salts and/or prodrugs thereof, and at least another of said pharmaceutical compositions comprises GA. In a particular embodiment, the kit of the invention comprises two separate pharmaceutical compositions, one of them comprising MTA and/or the pharmaceutically acceptable salts and/or prodrugs thereof, and the other of them comprising GA. The kit also comprises a container for said separate pharmaceutical compositions, such as a divided bottle or a divided foil packet. Illustrative non-limiting examples of containers include syringes, boxes, bags, and the like. A kit usually comprises indications for the administration of the separate components. The kit form is particularly advantageous when the separate components are preferably administered in different dosage forms (for example, oral and parenteral), are administered at different dosage intervals, or when the prescribing physician wishes to adjust the dose of the individual components of the combination.

The product of the invention or the kit of the invention is particularly suitable for the prevention and/or treatment of multiple sclerosis. In a particular embodiment, the product or the kit of the invention is used in the prevention and/or treatment of any form of MS, e.g., benign multiple sclerosis, RRMS, SPMS, PPMS or PRMS. In a preferred embodiment, the product of the invention or the kit of the invention is useful in the prevention and/or treatment of relapsing forms of MS, i.e., RRMS and PRMS. In a more preferred embodiment, the product of the invention or the kit of the invention is useful in the prevention and/or treatment of relapsing-remitting forms of MS, particularly RRMS. In a more preferred embodiment, the product of the invention or the kit of the invention is useful in the prevention and/or treatment of subjects with RRMS with the presence of one or more relapses after the treatment with GA alone for at least 1 month, 2 months, 3 months, 4 months, 5 months, 6 months, 7 months, 8 months, 9 months, 10 months, 11 months or 12 months. In another preferred embodiment, the product of the invention or the kit of the invention is useful in the prevention and/or treatment of subjects who suffer from MS and who have finished a therapy of mitoxantrone with GA.

An example of presentation of a kit of the invention is a blister pack. Blister packs are well known in the packaging industry and are widely used for packaging of pharmaceutical unit dosage forms (tablets, capsules, syringes, sterile powders, and the like). Blister packs generally consist of a sheet of relatively stiff material covered with a film of a preferably transparent plastic material. During the packaging process, recesses or cavities are formed in the plastic film. The recesses have the size and shape of the tablets or capsules to be packaged. Alternatively, the recesses or the cavities of the blister pack are conveniently manufactured to contain the injectable fluid medicament, or sterile powder to be reconstituted.

It may be desirable to provide a memory aid in the kit, for example, in the form of numbers next to the tablets, capsules, or injectable fluid whereby the numbers correspond with the days of the regimen on which the specified tablets or capsules should be ingested. Another example of said memory aid is a calendar printed on the card, for example, indicating "First Week, Monday, Tuesday, etc., Second Week, Monday, Tuesday," etc. Other variations of memory aids will be readily apparent. A "daily dose" can be a single tablet, capsule, or injectable fluid, or several pills, capsules, or injectable fluids to be taken on a given day. Furthermore, a daily dose of MTA and/or the pharmaceutically acceptable salts and/or prodrugs thereof can consist of several tablets or capsules, whereas a daily dose of GA can consist of a single injectable fluid and vice versa. The memory aid should reflect this and aid in the correct administration of the active agents.

In another aspect, the present invention relates to a dispenser designed to dispense the daily doses of each component (MTA and/or the pharmaceutically acceptable components and/or prodrugs thereof, and GA) one at a time, in the order of their intended use. The dispenser is preferably equipped with a memory aid, so as to further facilitate compliance with the dosage regimen. An example of said memory aid is a mechanical counter indicating the number of daily doses that have been dispensed. Another example of said memory aid is a battery-powered micro-chip memory coupled with a liquid crystal readout, or an audible reminder signal which, for example, reads out the date of the last daily dose that has been taken and/or reminds one when the next dose is to be taken.

In a particular embodiment, in the kit of the invention or in the product of the invention, the amount of GA may coincide with the therapeutically effective daily dose and may be comprised in the range from 10 to 80 mg, from 12 to 70 mg, from 14 to 60 mg, from 16 to 50 mg, from 18 to 40 mg, from 19 to 30 mg, or is approximately 20 mg. Alternatively, in another particular embodiment, the amount of GA in the kit of the invention or in the product of the invention may be comprised in the range from 50 to 150 mg, from 60 to 140 mg, from 70 to 130 mg, from 80 to 120 mg, from 90 to 110 mg, or is approximately 100 mg.

For each amount of GA in the kit of the invention or in the product of the invention, the amount of MTA and/or the pharmaceutically acceptable salts and/or prodrugs thereof, in the same kit or product may be from 0.01 mg to 50 g, from 0.02 mg to 40 g, from 0.05 mg to 30 g, from 0.1 mg to 20 g, from 0.2 mg to 10 g, from 0.5 mg to 5 g, from 1 mg to 3 g, from 2 mg to 2 g, from 5 mg to 1.5 g, from 10 mg to 1 g, from 10 mg to 500 mg.

MTA and/or the pharmaceutically acceptable salts and/or prodrugs thereof and GA can be administered to a subject either orally, rectally, parenterally, (for example, intravenously, intramuscularly, or subcutaneously, etc.) intracisternally, intravaginally, intraperitoneally, intravesically, locally (for example, by means of powders, ointments or drops), or as a buccal or nasal spray.

The pharmaceutical compositions of the invention, suitable for their parenteral injection, include physiologically acceptable sterile aqueous or non-aqueous solutions, dispersions, suspensions or emulsions, or may comprise sterile powders for reconstitution into sterile injectable solutions or dispersions. Examples of suitable aqueous or non-aqueous carriers, diluents, solvents or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate.

The pharmaceutical formulations, particularly those comprising GA, may also include pharmaceutically acceptable adjuvants or carriers known to persons skilled in the art. Said adjuvants include complete Freund's adjuvant and incomplete Freund's adjuvant. The pharmaceutical compositions provided by this invention may also comprise wetting agents, emulsifying and suspending agents, sweetening agents, flavoring agents, coloring agents, perfuming agents and preservatives. Prevention of microorganism contamination of the formulations can be carried out by means of the addition of several antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical formulations can be brought about by means of the use of agents capable of delaying absorption, for example, aluminum monostearate and/or gelatin.

GA may be formulated in pharmaceutical compositions with pharmaceutically acceptable carriers, such as water, saline, and may be formulated in eye drops. GA may also be formulated in release systems, such as matrix systems.

Solid dosage forms for oral administration include capsules, tablets, powders, and granules. In said solid dosage forms, the active compound is admixed with at least one inert usual excipient (or carrier) such as sodium citrate or dicalcium phosphate or (a) fillers or extenders, such as for example, starches, lactose, sucrose, mannitol, or silicic acid; (b) binders, such as for example, carboxymethylcellulose, alginates, gelatin, polyvinylpyrrolidone, sucrose, or acacia; (c) humectants, such as for example, glycerol; (d) disintegrating agents, such as for example, agar-agar, calcium carbonate, potato or tapioca starch, alginic acid, certain complex silicates, or sodium carbonate; (e) solution retarding agents, such as for example, paraffin; (f) absorption accelerators, such as for example, quaternary ammonium compounds; (g) wetting agents, such as for example, cetyl alcohol or glycerol monostearate; (h) adsorbents, such as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid formulations of a similar type may also be used as fillers in soft or hard filled gelatin capsules using excipients such as lactose or milk sugar, as well as high molecular weight polyethylene glycols, and the like.

Solid dosage forms such as coated tablets, capsules and granules can be prepared with coatings or shells, such as enteric coatings and others known in the art. They may also contain opacifying agents, and can be formulated such that they release the active ingredient or ingredients in a delayed manner. Examples of embedding formulations that can be used are polymeric substances and waxes. The active ingredients can also be in micro-encapsulated form, if appropriate, with one or more of the aforementioned excipients.

Liquid dosage forms for oral administration include pharmaceutically acceptable emulsions, solutions, suspensions, syrups, and elixirs. In addition to the active ingredients, the liquid dosage form may contain inert diluents commonly used in the art, such as water or other solvents, solubilizing agents and emulsifiers, such as for example, ethyl alcohol, isopropyl alcohol, ethyl carbonate, ethyl acetate, benzyl alcohol, benzyl benzoate, propylene glycol, 1,3-butylene glycol, dimethylformamide, oils, particular cottonseed oil, groundnut oil, corn germ oil, olive oil, castor oil, sesame seed oil, Miglyol®, glycerol, tetrahydrofurfuryl alcohol, polyethylene glycols, fatty acid esters of sorbitan, or mixtures of these substances, and the like. In addition to said inert diluents, the formulation can also include adjuvants, such as wetting agents, emulsifying and suspending agents, sweetening agents, flavoring agents and perfuming agents.

Suspensions, in addition to the active ingredient or ingredients, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

The following examples are intended to illustrate the present invention and not to limit it.

EXAMPLE 1

Analysis of the Administration of MTA and GA to an MS Animal Model

This example was carried out to evaluate whether the administration of MTA and GA (Copaxone®) to an MS animal model could have a synergistic effect. The studies were approved by the Committee on Animal Care of the University of Navarre.

I. Materials and Methods

Animals

Female C57/bl6 mice from Charles River, which were 6-8 weeks old and had a body weight of 20 g, were used to obtain an MS animal model (acute EAE model) generated by immunization with a recombinant fragment of the mouse oligodendrocyte glycoprotein (rMOG35-55), which mice were housed in plastic cages and were given commercial food pellets and water ad libitum.

EAE Induction and Score

The mice were immunized in the base of both hind paws with 100 μl of an emulsion of equal volumes of saline and incomplete Freund's adjuvant (IFA) containing 300 μg of mouse MOG35-55 (Sigma) and supplemented with 5 mg/ml *Mycobacterium tuberculosis* (H37Ra strain) (Difco). Subsequently, 500 g of pertussis toxin (Sigma) were administered intraperitoneally (i.p) 24 hours and 72 hours after the immunization.

The animals were weighed and inspected daily to observe the onset of clinical signs of disease (EAE) by a blinded observer. The severity of the disease (EAE) was evaluated according to the following scale: 0=normal; 0.5=mild limp tail; 1=limp tail; 2=mild paraparesis of the hind limbs, unsteady gait; 3=moderate paraparesis, although voluntary movements are still possible; 4=paraplegia or tetraparesis; 5=moribund state.

Treatment

5'-methylthioadenosine (MTA) was prepared by Enantia Inc. (Barcelona, Spain) and purified following a previously described method [Schlenk F. et al., Arch. Biochem. Biophys. (1964), 106:95-100]. The animals were treated with MTA (96 mmol/kg of body weight=27.84 mg of MTA/kg of body weight) or placebo (100 mM Tris buffer, pH 7.0) by means of a daily i.p injection starting after immunization.

Glatiramer acetate (GA) was obtained from Teva Pharmaceutical Industries (Petah Tiqva, Israel) and it was applied by means of a daily i.p injection of 100 μl of 0.5 mg/ml (0.1 mg/mouse/day).

On the same day of EAE induction (immunization with rMOG35-55), the animals were randomly divided into four groups, according to the treatment to be received, specifically, treatment with (i) placebo (n=6), (ii) MTA (n=5), (iii) GA (n=5) or (iv) MTA+GA (n=5). In each case, the treatment was administered daily and the animals were evaluated blindly.

Tissue Samples

At the end of the study (day 31 after immunization), the animals were anaesthetized and perfused intracardially with 4% paraformaldehyde in 0.1 M of phosphate buffer (pH 7.6). Brains and segments of cervical, thoracic, and lumbar spinal cord were dissected and fixed overnight. After incubation in 5% sucrose overnight at 4° C., the tissue was embedded in paraffin to conduct the histopathology and immunohistochemistry studies.

Statistical Analyses

The statistical analyses were conducted with the two-sided Mann-Whitney test to compare the EAE scores, the $\chi^2$ test to compare the incidence of the disease, and Kaplan Meier curves for differences in the day of onset of acute EAE or differences in the onset of the second relapse in chronic-relapsing EAE. Values of P<0.05 were considered to indicate a significant difference. The statistical evaluation was carried out by using the SPSS 11.0 statistical program.

II. Results

As has been previously mentioned, beginning on the same day of induction of EAE, the animals were randomly assigned to daily treatment with placebo, MTA, GA, or MTA+GA, and evaluated blindly.

The animals treated with placebo (n=6) developed neurological symptoms of chronic EAE consisting of progressive weight loss, limp tail, and mild to moderate paraparesis.

The animals treated with MTA (n=5) and the animals treated with GA (n=5) showed a course of the disease with intermediate intensity.

Finally, the animals treated with GA and MTA (n=5) experiences the virtual suppression of the disease.

In addition to the immunomodulatory activity that MTA has alone, the obtained results indicate that the joint administration of MTA and GA has a synergistic effect in the suppression of brain autoimmunity in the EAE model. These results show that the combination therapy of MTA and GA produces an increased benefit for patients who suffer from MS when compared to current therapies in which GA alone is administered.

The invention claimed is:

1. A combination comprising
   (A) 5'-methylthioadenosine and/or the pharmaceutically acceptable salts and/or prodrugs thereof, and
   (B) glatiramer acetate.

2. Combination according to claim 1, further comprising one or more additional compounds useful in the treatment of multiple sclerosis.

3. A pharmaceutical composition comprising an effective amount of a combination according to claim 1, and a pharmaceutically acceptable excipient.

4. A pharmaceutical composition comprising an effective amount of a combination according to claim 2, and a pharmaceutically acceptable excipient.

5. A product comprising:
   (A) 5'-methylthioadenosine and/or the pharmaceutically acceptable salts and/or prodrugs thereof, and
   (B) glatiramer acetate,
as a combined preparation for the simultaneous, separate or sequential use of said components (A) and (B).

6. A method for the prevention and/or treatment of multiple sclerosis comprising administering to a subject in need thereof a therapeutically effective amount of a combination according to claim 1.

7. Method according to claim 6, wherein the multiple sclerosis to be prevented and/or treated is a relapsing form of multiple sclerosis.

8. Method according to claim 6, wherein the multiple sclerosis to be prevented and/or treated is a relapsing-remitting form of multiple sclerosis.

9. Method according to claim 6, wherein the multiple sclerosis to be prevented and/or treated is a relapsing-remitting form of multiple sclerosis with the presence of one or more relapses after having been treated with glatiramer acetate alone for at least 1 month.

10. Method according to claim 6, wherein said subject is a subject who suffers from multiple sclerosis and has finished a therapy of mitoxantrone with glatiramer acetate.

* * * * *